US006984992B1

(12) United States Patent
Whitten (10) Patent No.: US 6,984,992 B1
(45) Date of Patent: Jan. 10, 2006

(54) CONDOM TESTING APPARATUS

(75) Inventor: James R. Whitten, Albany, GA (US)

(73) Assignee: Agri Dynamics, Inc., Albany, GA (US)

( * ) Notice: Subject to any disclaimer, the term of this patent is extended or adjusted under 35 U.S.C. 154(b) by 0 days.

(21) Appl. No.: 10/886,197

(22) Filed: Jul. 7, 2004

(51) Int. Cl.
*G01N 27/00* (2006.01)
(52) U.S. Cl. ..................................... 324/558; 324/557
(58) Field of Classification Search ................ 324/558, 324/559, 517
See application file for complete search history.

(56) References Cited

U.S. PATENT DOCUMENTS

| | | | |
|---|---|---|---|
| 2,221,323 A | 11/1940 | Gammeter | 209/571 |
| 2,609,094 A | 9/1952 | Fry | 209/10 |
| 2,649,960 A | 8/1953 | Gammeter | 209/572 |
| 5,499,898 A * | 3/1996 | Vonier et al. | 414/755 |
| 6,160,406 A | 12/2000 | Underwood et al. | 324/558 |

* cited by examiner

*Primary Examiner*—Anjan Deb
*Assistant Examiner*—John Teresinski
(74) *Attorney, Agent, or Firm*—Thomas C. Saitta (57) ABSTRACT

A condom testing apparatus having a plurality of electrically conductive mandrels having condoms loaded thereon, a first set of condom-contacting electrode members, a second set of condom-contacting electrode members, and a gapped electrical circuit between each of the mandrels and the first set of condom-contacting electrode members and between each of the mandrels and the second set of condom-contacting electrode members during testing, wherein defects within a condom being tested are detected by passage of current between the mandrels and the first and second sets of condom-contacting electrode members, wherein the first set of condom-contacting electrode members contacts less than 100 percent of the circumference of each of the condoms and the second set of condom-contacting electrode members contacts less than 100 percent of the circumference of each of the condoms, such that two condoms can be tested at once.

35 Claims, 5 Drawing Sheets

CONDOM TESTING APPARATUS

BACKGROUND OF THE INVENTION

This invention relates generally to the field of machines, equipment or apparatuses used to test condoms for holes, excessively thin walls or other imperfections prior to packaging and distribution. More particularly, the invention relates to such machines, equipment or apparatuses that utilize electrical current to determine the presence of such imperfections.

Minute holes, tears, or excessively thin wall areas subject to failure during use are unacceptable and render a condom defective. By virtue of their intended use, it is absolutely essential that condoms provide a complete and impermeable barrier. Minute holes undetectable under visual inspection and excessively thin spots in the condom wall likely to fail in use must be discovered. Because the manufacturing process produces huge numbers of condoms at a high rate and because the material of construction, typically a latex or similar plastic, is purposely very thin and elastic, there is always likely to be a relatively small number of defective products in any production run. Because of this, every condom must be tested prior to packaging and distribution for sale to insure that no defective condoms are supplied to consumers.

One method to detect defective condoms is to utilize air or a vacuum, wherein the passage of any air or gas through the condom wall is detected and indicates a defect. A second method utilizes water to test for defects. Typically this involves placing the condom on an electrically conductive mandrel, immersing the condom in water containing an electrical lead and then attempting to pass a current through the water to the mandrel. The condom material acts as an insulating barrier between the water and the mandrel to prevent completion of the electrical circuit, but any hole in the condom will allow the circuit to be completed, indicating that the condom is defective. Advantages of this technique are that low electrical voltages are required and the use of water as a conductive medium provides full contact to all portions of the condom. The major drawback to this technique is that the condoms must be dried prior to packaging. Another drawback is that the technique does not provide an indication of excessively thin spots in the condom wall which may tear in use, since the thin material is still sufficient to prevent passage of current from the water to the mandrel.

A third method, and the method utilized in this invention, also takes advantage of the fact that the condom is an electrical insulator. The condom is placed onto a metal, i.e., electrically conductive, mandrel and the outer surface of the condom is then brought into contact with another electrically conductive member, such as a metal mesh, a pad or bristles. In some instances, the condoms are wetted prior to testing, although this is not preferred for the reasons set forth above. The condom prevents completion of a closed circuit to ground, unless there is a defect, in which case the current will arc through the hole, tear or thin-walled area and complete the circuit. This completed circuit indicates a defective condom, which is then discarded. When a conductive mesh material is utilized, the mesh is constructed so as to be very non-rigid so that it closely drapes against the condom on the conductive mandrel. The mandrel and condom are rotated while contacting the electrified mesh, and any defects will allow the current to pass through the condom to the mandrel. A problem with this technique is that because the mesh must have a large amount of open area to achieve the desired flexibility, direct contact against every portion of the condom is not achieved, so a relatively high and thus dangerous amount of electrical current must be used—typically greater than 50 watts—to try to insure that the current will arc from the mandrel through a defect to the nearest piece of mesh. The variation in distance from the condom to particular points on the mesh as the condom is moved past the mesh also makes proper calibration of the electrical current difficult. Another problem is presented by the nipple portion of the condom. Because of this change in configuration from the generally cylindrical main body portion of the condom, providing sufficient contact between the mesh and the nipple material is problematic and defects can be missed. Examples of testing equipment that utilizes this methodology are shown in U.S. Pat. No. 2,221,323 to Gammeter, U.S. Pat. No. 2,609,094 to Fry, and U.S. Pat. No. 2,649,960 to Gammeter.

An improved method and apparatus that utilizes completion of an electrical current to indicate defects in a condom, but which does not utilize a mesh material as one of the electrodes, is shown in U.S. Pat. No. 6,160,406 to Underwood et al., the disclosure of which is incorporated herein by reference. The exterior condom-contacting members comprise in combination an electrically conductive fabric member and an electrically conductive brush member, and may also comprise only fabric members or only brush members. For the combination fabric and brush assembly, the fabric member is positioned to contact the generally cylindrical main body portion of the condom as it is brought across the fabric member. The fabric member is sufficiently long in the mandrel direction of travel such that the condom is tested over its full circumference of 360 degrees, and preferably is provided excessively long such that more than one revolution of the condom is achieved during the test pass. The fabric member is not positioned to contact the far end of the nipple portion, as the friction from the rotational movement would twist and damage the condom. The brush member is positioned along the nipple portion, preferably at an angle to the central axis of the rotating mandrel, in order to contact the extreme end of the nipple portion. In this manner every point of the condom is in direct contact with either the conductive fabric member or the conductive brush member, such that the electrical current will complete the circuit through any minute hole in the condom to indicate a defective condom. Furthermore, because the contact between the condom and both the fabric member and brush member is so extensive, and because the fabric member and brush member are positioned relatively close to the mandrel and at a relatively constant distance, the current strength can be adjusted such that the circuit will be completed even through excessively thin-walled areas of the condom, thus indicating a defective condom even where a hole is not present initially. Alternatively, the fabric member may be omitted and the condom-contacting means formed entirely of one or more conductive brush members appropriately arranged to contact the full extent of the exposed condom on the mandrel. In this construction means such as a geared or friction mechanism are required to rotate the mandrel as it is passed across the brush member, since the coefficient of friction between the brush members and the mandrel would be insufficient to rotate the mandrel unaided.

It is common in testing equipment of the various types described above to mount a plurality of mandrels onto a rotating table, track or platform in a circular pattern. With this construction, it is possible to provide a loading station, a testing station and a removal station, each spaced along the travel pathway of the mandrels, such that the table can be rotated continuously in a single direction. The condoms are individually loaded onto empty mandrels, which then travel through the testing zone to identify any defective condoms. The condoms are then removed from the mandrels, with the defective condoms being separated and discarded. Loading of the condoms onto the mandrels may be accomplished manually or by automated equipment. Likewise, removal of the condoms may be accomplished manually or by automatic equipment, although the use of automatic removal and separating equipment in communication with the testing equipment is typical. Loading, removal and separating equipment of various types are well known in the art.

In this type of condom defect testing equipment, the minimum distance between adjacent mandrels on the platform, table or track is determined by the circumference of the test mandrels themselves. A typical mandrel may be approximately 5.81 inches in circumference, as it is necessary to provide a uniform stretch on the condom during testing. Since the known condom testing equipment utilizes a single electrically conductive mesh, pad or brush to test each individual condom, with the condom and mandrel being rotated in excess of 360 degrees as it travels across the electrically conductive mesh, pad or brush, the length of the mesh, pad or brush in the mandrel travel direction must be of a distance in excess of the circumference of the loaded mandrel. In practice, this length dimension must also include an additional distance beyond the mandrel circumference as a safety factor to insure that the complete circumference of each condom is tested, so that typically at least 125 percent of the circumference is tested. Since more than one condom cannot be in contact with the mesh, pad or brush during a given test procedure, the mandrels must also be separated a distance greater than the length of the testing mesh, pad or brush. This separation requirement limits the number of mandrels that can be positioned on the rotating table, which in turns limits the testing rate for the condoms. In a typical automatic loading test apparatus, for example, the mandrels are typically separated a distance of approximately 10 inches and the maximum travel rate or rate of rotation is about 12 inches per second.

Because the maximum travel rate is limited, especially with regard to manual loading, an apparatus that enables the mandrels to be more closely spaced will increase the number of condoms that can be tested over a given time period. Condom testing equipment with automatic condom loading typically test about 100 condoms per minute, while manually loaded testing equipment typically test about 50 to 60 condoms per minute. While increasing the testing rate of either type is desirable, the manual loading test equipment is much cheaper and occupies significantly less floor space than automatic loading test equipment, and thus it is especially desirable to increase the testing rate on the manual loading apparatuses.

It is an object of this invention to provide an improved condom testing apparatus and methodology which address the problems described above in terms of increasing the testing rate of condoms, especially with regard to manual loading condom testing apparatuses, in that the distance between condom-containing mandrels is minimized. It is an object to provide such an apparatus wherein the defects in a condom are detected upon passage of an electrical current between an electrically conductive mandrel and multiple external condom-contacting electrode members through any defect in the condom such that a closed circuit is formed. It is an object to provide such an apparatus wherein the length of any of the condom-contacting electrode members in the direction of travel of the mandrel is less than the circumference of the mandrel, such that at least two sets of condom-contacting electrode members are required to test the entire circumference of the condom, in that neither set of condom-contacting electrode members individually tests the full circumference of the condom. It is an object to provide such an apparatus wherein a second condom-containing mandrel is tested on the first set of condom-contacting electrode members simultaneously with a first condom-containing mandrel being tested on the second set of condom-contacting electrode members, the first condom-contacting mandrel having been already tested on the first set of condom-contacting electrode members and advanced to the second set of condom-contacting electrode members. These objects, as well as objects not expressly set forth, will be apparent upon examination of the disclosure that follows.

SUMMARY OF THE INVENTION

The invention is in general a condom defect testing apparatus that utilizes electrical current to detect holes, tears or excessively thin-walled areas in a condom, wherein the non-defective condom acts as an insulator to prevent current flow between external condom-contacting electrode members and a conductive mandrel electrode member. If the electrical circuit containing any one of the condom-contacting electrode members and the conductive mandrel is closed due to the arcing of current through a defect, this state is detected and the condom is deemed defective and is subsequently discarded. The mandrels are mounted onto a rotating platform, track or table, typically such that the travel path is circular, whereby the condoms are loaded onto the mandrels at a loading station, the loaded mandrels are passed through a testing zone in which the condoms are identified as being defective or non-defective, the condoms are removed from the mandrels in a stripping station, with the defective condoms being separated from the non-defective condoms, and the empty mandrels are returned to the loading station. The rotation of the platform, track or table is preferably a continuous rotation, although an indexed rotation would also be possible.

In order to minimize spacing of the test mandrels for the purpose of increasing the testing rate, at least two sets of condom-contacting electrode members are provided, wherein each individual set of condom-contacting electrode members tests less than the full 360 degree circumference of the condom mounted on the mandrel. Each condom is passed through a testing zone containing the at least two sets of condom-contacting electrode members, and the mandrel is rotated as it passes through the testing zone. In an embodiment wherein there are two sets of condom-contacting electrode members, each set tests between 360 and 180 degrees of the condom circumference, and the sets are spaced along the mandrel travel direction such that sufficient rotation of the mandrel occurs during travel from the first set to the second set to insure that the tested portions of the condom circumference overlap. Because the sets of condom-contacting electrode members are spaced, a second condom loaded mandrel is tested on the first set of condom-contacting electrode members simultaneously with a first condom loaded mandrel being tested on the second set of condom-contacting electrode members, thereby allowing the mandrels to be more closely spaced.

The sets of condom-contacting electrode members each comprise at least a condom body contacting member and a condom nipple contacting member, wherein preferably the condom body contacting member comprises an electrically conductive fabric or pad member and the condom nipple contacting member comprises an electrically conductive brush member. Most preferably three condom body contacting members are provided, a pair of such condom body contacting members, preferably conductive pads or fabric members, being separated perpendicularly relative to the mandrel axis of rotation, with an additional condom body contacting member, preferably a conductive brush member, being disposed on the opposing side of the mandrel along with the condom nipple contacting member in order to test the area of the condom corresponding to the gap between the two condom opposing condom body contacting members. With this construction, different amounts of current may be passed through the independent condom body contacting members to account for variations in wall thickness in the condom body.

DETAILED DESCRIPTION OF THE INVENTION

With reference to the drawings, the invention will now be described in detail with regard for the best mode and the preferred embodiment. For purposes of this disclosure, the invention will be arbitrarily described such that the central axes of the mandrels are oriented vertically with the nipple end of the mandrel and condom on top, and such that the mandrels are positioned on a platform that rotates or moves horizontally, such that any references to relative direction are based on this construct. Furthermore, in this disclosure the individual mandrels are described as rotating clockwise and the platform as rotating clockwise. It is understood, however, that the orientation and rotation directions of the condom defect testing apparatus may be varied without departing from the scope of the claimed invention.

In general, the invention is a condom defect testing apparatus for testing individual condoms 50 for defects, such as holes, tears or thin-walled regions susceptible to failure during use, such that any defective condoms 50 are identified and destroyed prior to packaging and distribution. The testing apparatus is utilized in conjunction with condom loading means for mounting individual condoms 50 onto test mandrels 40 and condom removal and sorting means for removing the condoms 50 from the mandrels 40 and separating the defective condoms from the non-defective condoms. The condom loading means may comprise mechanical apparatuses for automatically mounting the condoms 50 on the mandrels 40, or the condoms 50 may be loaded onto the mandrels 40 manually. The condom removal and sorting means may also be automatic or manual, but automatic systems in communication with the defect testing apparatus are most common. In a representative removal and sorting system, a roller is used to roll up the condom 50 and a pair of brushes are used to knock the condom 50 off the mandrel 40, one brush being activated for a defective condom 50 and a different brush being activated for a non-defective condom 50, such that the defective condoms 50 are expelled into separate conveyors or bins. Thus, the condom defect testing apparatus as contemplated may be incorporated into existing systems or the apparatus may comprise a complete system comprising the condom loading means, the testing means as described in detail herein, and the removal and sorting means.

Electrically conductive mandrels 40 are known in the condom testing art, and a typical mandrel 40 comprises a base 41, a cylindrical extended body 42 and a nipple end 43, the nipple end 43 comprising a transitional shoulder reducing the diameter of the mandrel 40 down to a smaller tip. The shape of the mandrel 40 is chosen such that a condom 50 comprising a body 51 and a nipple end 52 is uniformly stretched when loaded onto the mandrel 50. Mandrel mounting means 42 join the mandrels 40 to a moving platform, track or table member 45, wherein the mandrel mounting means 42 allows each mandrel 40 to rotate about its central axis, and wherein the platform member 45 is typically rotated by a motor such that the travel pathway 99 of the mandrels 40 is circular. Mandrel mounting means 42 may comprise for example a cylindrical pin member mounted below the base 41 that is received by a bore disposed in the rotating platform member 45. Mandrel rotating means 46 is provided to rotate the individual mandrels 40 about their central axes, and may comprise a curved member that interacts frictionally or mechanically interfaces with the base 41 of the mandrel 40 as it is brought through the testing zone, such that controlled rotation of each mandrel 40 is achieved as it proceeds along the mandrel travel pathway 99.

Figure 2:
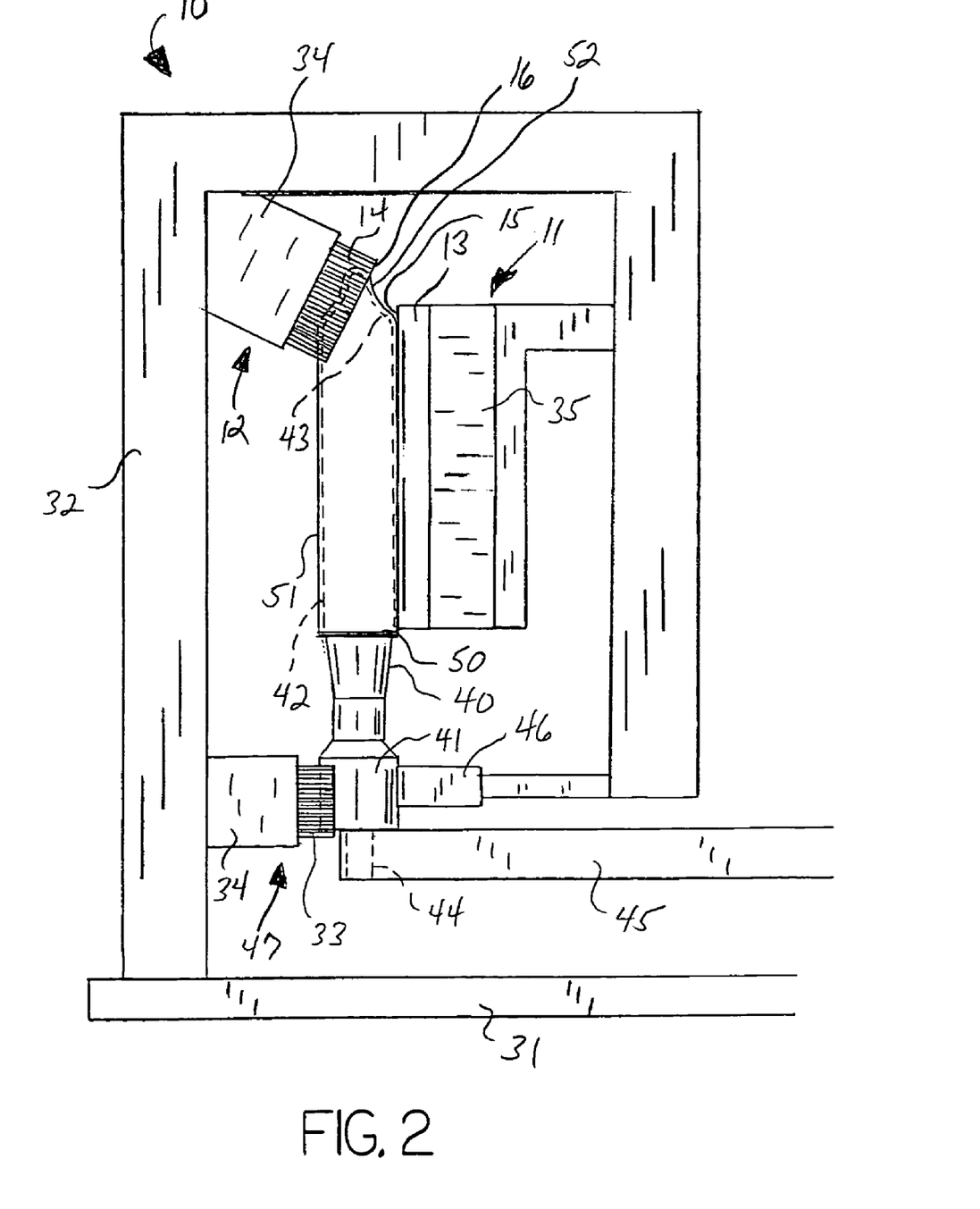
FIG. 2 is a side view of the invention showing one set of the condom-contacting electrode members and the mandrel-contacting electrode member.
Figure 3:
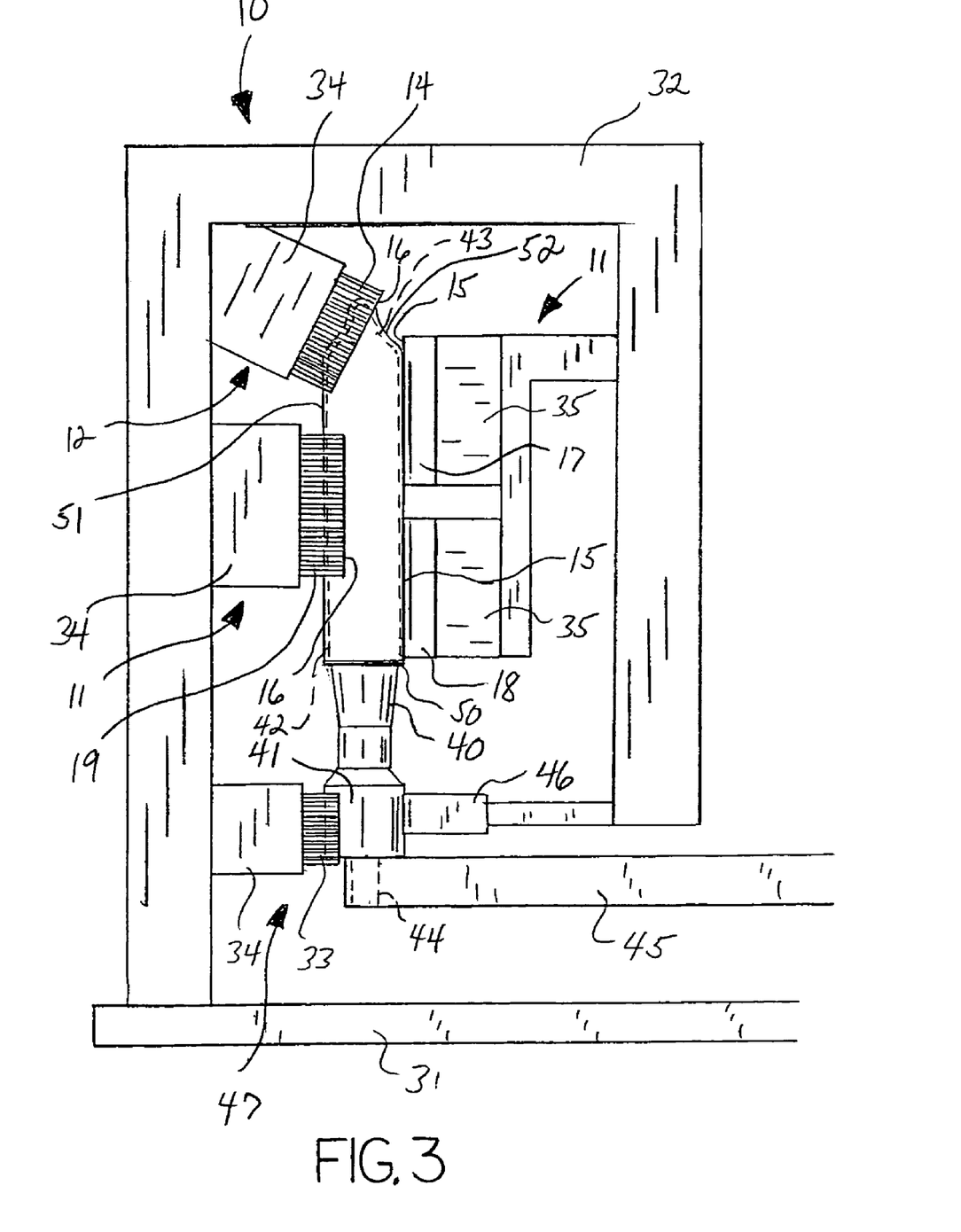
FIG. 3 is a side view of the invention similar to FIG. 2 but showing an alternative embodiment having one set of the condom-contacting electrode members comprising a pair of conductive pad members and an additional brush member.
Figure 4:
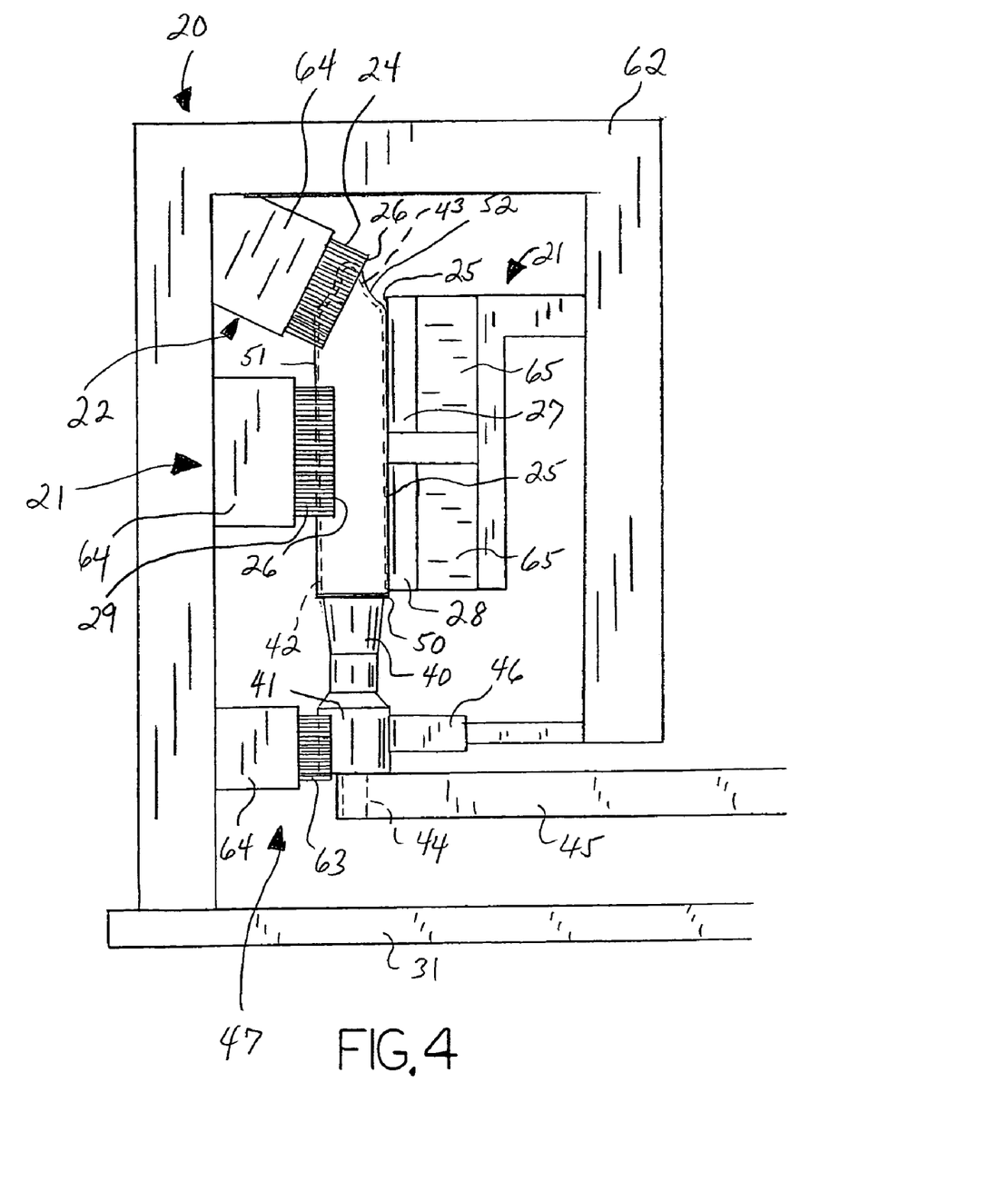
FIG. 4 is a side view similar to FIG. 3, showing a second set of condom-contacting electrodes

Mandrel contacting electrode means 47 are provided such that each mandrel 40 is a component in the electrical testing circuitry of the condom defect testing apparatus, the particular electrical conductors and pathways for the testing circuitry being a matter of engineering choice well within the scope of those skilled in the art. A suitable design for the testing circuitry involves connecting the test mandrels 40 to ground via the mandrel contacting electrode means 47, such that any current passing through a defect in a condom 50 closes the circuit, which state is then detected in known manner. As shown in FIGS. 2 through 4, a suitable embodiment for the mandrel contacting electrode means 47 comprises an electrically conductive grounding brush member 33 or 63 mounted by brush mounting means 34 or 64 to a framework 32 or 62 connected to a base 31, respectively. As the mandrel 40 is brought through the testing zone, the conductive brush member 33 or 63 remains in contact with the mandrel base 41, the brush member 33 or 63 extending longitudinally in the mandrel travel direction approximately the same distance as the condom body contacting means 11 or 21 and the condom nipple contacting means 12 or 22, respectively. For a circular pathway 99 as illustrated, it is preferred that the contact surface of the grounding brush member 33 or 63 be curved equivalent to the circular arc of the mandrel travel pathway 99.

The condom defect testing apparatus comprises a first set of condom-contacting electrode members 10 and at least a second set of condom-contacting electrode members 20, with the condom body contacting means 21 and condom nipple contacting means 22 of the second set 20 being physically separated from the condom body contacting means 11 and condom nipple contacting means 12 of the second set 10, such that a gap is defined along the travel pathway 99 during which a mandrel 40 and condom 50 are in contact with neither the first set 10 nor the second set 20 in the middle of the testing zone, thereby defining a first testing stage and a second testing stage. The first set of condom-contacting electrode members 10 comprises condom body contacting means 11 and condom nipple contacting means 12 that are components in the electrical testing circuitry whereby a current may independently pass from either the condom body contacting means 11 or the condom nipple contacting means 12 through a defect in the condom 50 and into the mandrel 40 to ground, thereby closing or completing the electrical circuit, which status is then detected by electrical circuit status sensing means as indication that the condom 50 being tested is defective, the status sensing means then operatively determining the sorting of the condom 50 upon removal from the mandrel 40. The design of the particular electrical conductors, pathways and status sensing means for the testing circuitry are a matter of engineering choice well within the scope of those skilled in the art.

The condom body contacting means 11 preferably comprises a single or plural electrically conductive pad member 13, typically formed of an electrically conductive fabric material backed by a compressible internal member. The conductive pad member 13 is mounted to a framework 32 such that the condom body contacting means 11 remains stationary as the loaded mandrel 40 is passed through the first testing stage. The pad contact surface 15 is curved so as to correspond to the travel pathway 99, such that the pressure applied to the condom 50 remains generally uniform as it passes. The rotational rate of the mandrel 40 is set to match the travel speed of the mandrel along the pathway 99 such that the frictional contact between the pad contact surface 15 and the condom body 51 does not shift the condom 50 on the mandrel 40 nor stretch the condom body 51. The height of the conductive pad member 13 must be sufficient to contact the majority of the condom body 51.

In the preferred embodiment, as shown in FIG. 3, conductive pad member 13 comprises an upper pad member 17 and a lower pad member 18, physically separated by a horizontally oriented gap. This allows the current passing through the upper pad member 17 to be set at a different level from the current passing through the lower pad member 18, which provides better results for condoms 50 wherein the upper portion of the condom body 51 has a different shape or wall thickness than the lower portion of the condom body 51. When multiple pad members 17 and 18 are present, the condom body contacting means 11 further comprises an electrically conductive body brush member 19 located opposite from the pad members 17 and 18, with the body brush member 19 being vertically positioned to cover and exceed the gap area between the pad members 17 and 18. In this manner the full longitudinal length of the condom body 51 is tested by the combination of the condom body contacting pad members 17 and 18 and the body brush member 19.

The nipple end 52 of the condom 40, which includes the transitional shoulder portion, is tested for defects by condom nipple contacting means 12, which preferably comprises an electrically conductive brush member 14 mounted on the framework 32 on the opposite side from the body contacting means 11. The brush contact surface 16 extends from the top of the nipple end 52, past the transition shoulder and overlaps a portion of the upper end of the condom body 51 so that a portion of the condom body 51 is tested by both the condom nipple contacting means 12 and by the condom body contacting means 11. Preferably the brush contact surface 16 is curved to correspond to the arc of the mandrel travel pathway 99.

The horizontal or longitudinal dimension of the condom body contacting means 11, i.e., the contact surface 15 the pad member 13 or the combined pad members 17 and 18, and the horizontal or longitudinal dimension of the condom nipple contacting means 12, i.e., the contact surface 16 of the brush member 14, in the direction along the mandrel travel pathway 99, is less than the distance around the circumference of the mandrel 40. In this manner, the condom nipple contacting means 12 and by the condom body contacting means 11 of the first set of condom-contacting electrode members 10 will test less than 100 percent of the surface of the condom 50 as the mandrel 40 passes through the first test stage. For example, for a mandrel having a diameter of approximately 1.85 inches and therefore a circumference of approximately 5.81 inches, the longitudinal dimensions of the contact surface 16 of the condom nipple contacting means 12 and the contact surface 15 of the condom body contacting means 11 cannot exceed 5.81 inches.

The condom defect testing apparatus further comprises a second set of condom-contacting electrode members 20 that are physically separated from the first set 10 and which define a second testing stage in the testing zone. The second set 20 comprises condom body contacting means 21 and condom nipple contacting means 22 which perform the functions equivalent to the corresponding means of the first set 10. Preferably, the components of the second set 20 correspond directly to the components of the first set 10, such that the second set 20 comprises a conductive pad member 23, or a pair of upper and lower conductive pad members 27 and 28, a conductive brush member 24, pad contact surface 25, brush contact surface 26, frame 62, brush mounting means 64 and pad mounting means 65, which are structurally and functionally equal or substantially similar to first set 10 components conductive pad member 13, or a pair of upper and lower conductive pad members 17 and 18, a conductive brush member 14, pad contact surface 15, brush contact surface 16, frame 32, brush mounting means 34 and pad mounting means 63. Such similarities are illustrated by comparing FIGS. 3 and 4. As with first set 10, the horizontal or longitudinal dimension of the condom body contacting means 21, i.e., the contact surface 25 the pad member 23 or the combined pad members 27 and 28, and the horizontal or longitudinal dimension of the condom nipple contacting means 22, i.e., the contact surface 26 of the brush member 24, in the direction along the mandrel travel pathway 99, must be less than the distance around the circumference of the mandrel 40.

Figure 5:
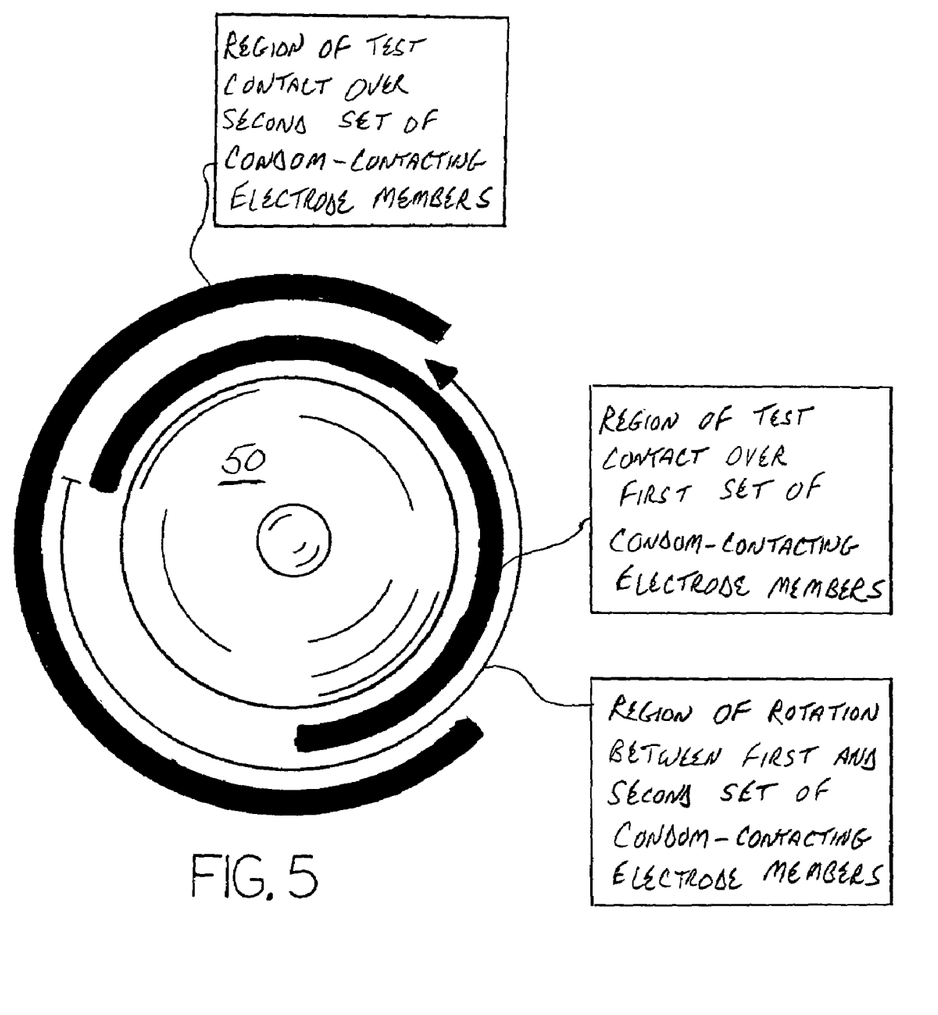
FIG. 5 is a schematic diagram illustrating rotation of the condom-loaded mandrel through the testing zone, showing the overlapping regions of contact with the condom-contacting electrode members such that greater than 360 degrees of condom circumference are tested.

The first set of condom-contacting electrode members 10 defining the first testing stage of the testing zone are separated from the second set of condom-contacting electrode members 20 defining the second testing stage of the testing zone a distance such that the rotation of the mandrel 40 about its central axis caused by the mandrel rotating means 46 will result in the area of the condom 50 not tested by the first set 10 to be tested by the second set 20, along with a region of overlap that is tested by both the first set 10 and second set 20, as shown in FIG. 5. For example, it has been found suitable to test approximately 260 degrees of the condom circumference on the first set of condom-contacting electrode members 10, provide a separation sufficient to allow for approximately 253 degrees of mandrel rotation between the first set 10 and the second set 20, and then test approximately 260 degrees on the second set of condom-contacting electrode members 20. Because the two testing stages overlap, more than 100 percent of the condom circumference is tested, with approximately 200 degrees of the condom circumference being tested once and approximately 160 degrees of the condom circumference being tested twice in the overlapping regions. It is of course possible to structure the first and second sets of condom-contacting electrodes 10 and 20 such that the amount of overlap is smaller, or wherein one of the sets 10 or 20 is longer than the other in the horizontal testing direction.

Figure 1:
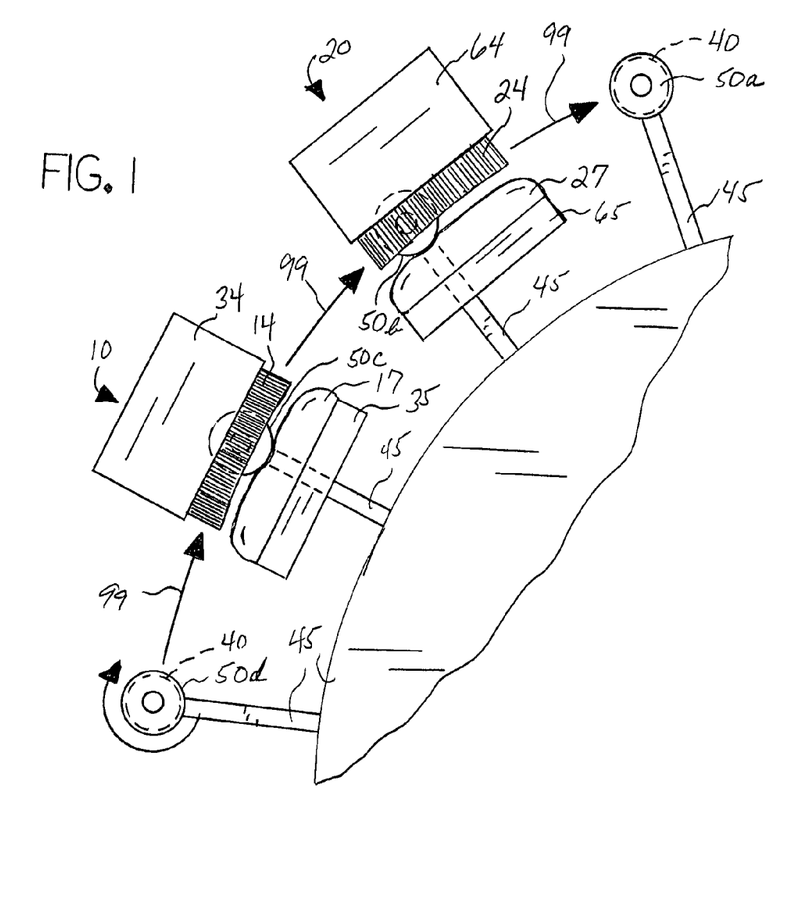
FIG. 1 is a vertical view of an embodiment of the condom testing apparatus, showing a portion of the rotating platform, wherein a tested condom-loaded mandrel has exited the testing zone, a first condom-loaded mandrel is being tested on the second set of condom-contacting electrode members, a second condom-loaded mandrel is being tested on the first set of condom-contacting electrode members, and a pre-testing condom-loaded mandrel is being advanced into the testing zone.

FIG. 1 shows a portion of the rotating platform member 45 having condoms 50*a*, 50*b*, 50*c* and 50*d* mounted on mandrels 50 rotatably mounted extended arms. Condom 50*a* has already passed through the testing zone and is ready to be removed and sorted. Condom 50*d* is about to enter the testing zone. Condom 50*b* is passing through the second set of condom-contacting electrode members 20, having already passed through the first set of condom-contacting electrode members 10. Under the example given above, approximately 260 degrees of the circumference of the condom 50*b* was tested in the first set 10, the mandrel 40 was rotated approximately 253 degrees prior to reaching the second set, and an overlapping 260 degrees is being tested in the second set 20. Condom 50*c* is passing through the first set of condom-contacting electrode members 10 and approximately 260 degrees of circumference is being tested. Because the first set 10 and second set 20 are separated, condom 50*c* can be tested at the same time as condom 50*b*, thereby allowing the distance between the mandrels 40 to be reduced, such that more condoms 40 will be tested in a given time period at the same rate of rotation of platform member 45.

As a representative example, a platform member 45 approximately 3.75 feet in diameter having mandrels 40 each with a circumference of approximately 5.81 inches may utilize a first set of condom-contacting electrode members 10 approximately 4.2 inches in longitudinal dimension along the mandrel travel pathway 99 and a second set of condom-contacting electrode members 10 approximately 4.2 inches in longitudinal dimension along the mandrel travel pathway 99, the first set 10 and second set 20 being separated approximately 4.1 inches along the mandrel travel pathway 99. With this construction, the mandrels 40 may be spaced approximately every 7.8 inches, which is a significant decrease over known testing apparatuses. On a manual loading machine, this increases the testing rate from about 50 to 60 condoms per minute to about 105 to 110 condoms per minute, while still allowing enough separation for manual loading and maintaining a platform rotational speed of about 12 inches per second.

While the invention has been described with reference to a first set 10 and a second set 20 of condom-contacting electrode members defining a first and second stage in the testing zone, it is understood that more than two sets of condom-contacting electrode members may be utilized in succession, with the dimensions in the longitudinal direction along the travel pathway 99 and the separation distance between sets being reduced for each as required to insure that multiple condoms 40 do not contact any given set simultaneously and that sufficient rotation occurs to insure the full circumference of each condom 50 is tested.

It is understood that equivalents to certain elements set forth above may be obvious to those skilled in the art, and therefore the full scope and definition of the invention is to be as set forth in the following claims.

I claim:

1. A condom testing apparatus comprising:
   a plurality of electrically conductive mandrels having condoms loaded thereon;
   a first set of condom-contacting electrode members;
   a second set of condom-contacting electrode members separated from said first set of condom-contacting electrode members such that no one of said condoms contacts both said first and said second sets of condom-contacting electrode members simultaneously;
   a gapped electrical circuit between each of said mandrels and said first set of condom-contacting electrode members and between each of said mandrels and said second set of condom-contacting electrode members during testing;
   means to sense the status of said electrical circuit between each of said mandrels and said first set of condom-contacting electrode members and between each of said mandrels and said second set of condom-contacting electrode members;
   wherein said first set of condom-contacting electrode members tests less than 100 percent of the circumference of each of said condoms and said second set of condom-contacting electrode members tests less than 100 percent of the circumference of each of said condoms.

2. The apparatus of claim 1, wherein said first set of condom-contacting electrode members comprises condom body contacting means and condom nipple contacting means.

3. The apparatus of claim 2, wherein said second set of condom-contacting electrode members comprises condom body contacting means and condom nipple contacting means.

4. The apparatus of claim 3, wherein said condom body contacting means of said first set of condom-contacting electrode members and said condom body contacting means of said second set of condom-contacting electrode members each comprises a conductive pad member.

5. The apparatus of claim 4, wherein said condom nipple contacting means of said first set of condom-contacting electrode members and said condom nipple contacting means of said second set of condom-contacting electrode members each comprises a conductive brush member.

6. The apparatus of claim 5, wherein said condom body contacting means of said first set of condom-contacting electrode members and said condom body contacting means of said second set of condom-contacting electrode members each comprises an upper pad member, a lower pad member, and a body brush member.

7. The apparatus of claim 6, further comprising mandrel rotating means to rotate each of said mandrels during contact with each of said first set of condom-contacting electrode members and said second set of condom-contacting electrode members.

8. The apparatus of claim 7, further comprising a rotating platform member, wherein said mandrels are mounted on said rotating platform member.

9. The apparatus of claim 8, further comprising condom loading means to load said condoms onto said mandrels, condom removal means to remove said condoms from said mandrels, and condom sorting means to sort said condoms depending on whether each of said condoms is detected to be defective.

10. A condom testing apparatus comprising:
   a plurality of electrically conductive mandrels having condoms loaded thereon;
   at least two sets of condom-contacting electrode members separated from each other such that no one of said condoms contacts both said sets of condom-contacting electrode members simultaneously;
   a gapped electrical circuit between each of said mandrels and each of said at least two sets of condom-contacting electrode members during testing;
   means to sense the status of said electrical circuit between each of said mandrels and each of said at least two sets of condom-contacting electrode members, wherein defective said condoms allow passage of electrical current between said mandrels and each of said at least two sets of condom-contacting electrode members, and wherein non-defective said condoms prevent passage of electrical current between said mandrels and each of said at least two sets of condom-contacting electrode members;
   wherein each of said at least two sets of condom-contacting electrode members contacts less than 100 percent of the circumference of each of said condoms during testing, and wherein in combination said at least two sets of condom-contacting electrode members contact greater than 100 percent of the circumference of each of said condoms during testing.

11. The apparatus of claim 10, wherein each of said at least two sets of condom-contacting electrode members is in contact with a different one of said condoms simultaneously.

12. The apparatus of claim 11, wherein said at least two sets of condom-contacting electrode members comprises:
   a first set of condom-contacting electrode members defining a first testing stage, said first set being disposed to contact each of said condoms as each of said mandrels travel past said first set; and
   a second set of condom-contacting electrode members defining a second testing stage, said second set being disposed to contact each of said condoms as each of said mandrels travel past said second set.

13. The apparatus of claim 12, wherein said first set of condom-contacting electrode members comprises condom body contacting means and condom nipple contacting means.

14. The apparatus of claim 13, wherein said second set of condom-contacting electrode members comprises condom body contacting means and condom nipple contacting means.

15. The apparatus of claim 14, wherein said condom body contacting means of said first set of condom-contacting electrode members and said condom body contacting means of said second set of condom-contacting electrode members each comprises a conductive pad member.

16. The apparatus of claim 15, wherein said condom nipple contacting means of said first set of condom-contacting electrode members and said condom nipple contacting means of said second set of condom-contacting electrode members each comprises a conductive brush member.

17. The apparatus of claim 16, wherein said condom body contacting means of said first set of condom-contacting electrode members and said condom body contacting means of said second set of condom-contacting electrode members each comprises an upper pad member, a lower pad member, and a body brush member.

18. The apparatus of claim 17, further comprising mandrel rotating means to rotate each of said mandrels during contact with each of said first set of condom-contacting electrode members and said second set of condom-contacting electrode members.

19. The apparatus of claim 18, further comprising a rotating platform member, wherein said mandrels are mounted on said rotating platform member.

20. The apparatus of claim 19, further comprising condom loading means to load said condoms onto said mandrels, condom removal means to remove said condoms from said mandrels, and condom sorting means to sort said condoms depending on whether each of said condoms is detected to be defective.

21. A condom testing apparatus comprising:
   a first set of condom-contacting electrode members;
   a second set of condom-contacting electrode members;
   a rotating platform;
   a plurality of electrically conductive mandrels mounted on said platform, each of said mandrels receiving a condom thereon for testing, whereby each of said condoms is brought into contact first with said first set of condom-contacting electrode members and second with said second set of condom-contacting electrode members, and wherein said mandrels are spaced on said platform member such that one of said condoms is in contact with said second set of condom-contacting electrode members at the same time that a second of said condoms is in contact with said first set of condom-contacting electrode members, such that two of said condoms are tested simultaneously;
   a gapped electrical circuit between each of said mandrels and said first set of condom-contacting electrode members and between each of said mandrels and said second set of condom-contacting electrode members during testing;
   means to sense the status of said electrical circuit between each of said mandrels and said first set of condom-contacting electrode members and between each of said mandrels and said second set of condom-contacting electrode members, wherein said condoms that are non-defective prevent passage of electrical current between said mandrels and said first and second sets of condom-contacting electrode members;
   wherein said first set of condom-contacting electrode members contacts less than 100 percent of the circumference of each of said condoms and said second set of condom-contacting electrode members contacts less than 100 percent of the circumference of each of said condoms, wherein the area of contact on each of said condoms of said second set of condom-contacting electrode members overlaps two areas of contact on each of said condoms of said first set of condom-contacting electrode members, such that every point on the circumference of each of said condoms is contacted by at least one of said first and said second sets of condom-contacting electrode members during testing.

22. The apparatus of claim 21, wherein said first set of condom-contacting electrode members comprises condom body contacting means and condom nipple contacting means.

23. The apparatus of claim 22, wherein said second set of condom-contacting electrode members comprises condom body contacting means and condom nipple contacting means.

24. The apparatus of claim 23, wherein said condom body contacting means of said first set of condom-contacting electrode members and said condom body contacting means of said second set of condom-contacting electrode members each comprises a conductive pad member.

25. The apparatus of claim 24, wherein said condom nipple contacting means of said first set of condom-contacting electrode members and said condom nipple contacting means of said second set of condom-contacting electrode members each comprises a conductive brush member.

26. The apparatus of claim 25, wherein said condom body contacting means of said first set of condom-contacting electrode members and said condom body contacting means of said second set of condom-contacting electrode members each comprises an upper pad member, a lower pad member, and a body brush member.

27. The apparatus of claim 26, further comprising mandrel rotating means to rotate each of said mandrels during contact with each of said first set of condom-contacting electrode members and said second set of condom-contacting electrode members.

28. The apparatus of claim 27, further comprising condom loading means to load said condoms onto said mandrels, condom removal means to remove said condoms from said mandrels, and condom sorting means to sort said condoms depending on whether each of said condoms is detected to be defective.

29. A method for testing condoms for defects comprising:
providing a plurality of electrically conductive mandrels, at least a first set of condom-contacting electrode members and a second set of condom-contacting electrode members, wherein said second set of condom-contacting electrode members is separated from said first set of condom-contacting electrode members such that a condom cannot contact both said first and said second set of condom-contacting electrode members simultaneously, a gapped electrical circuit between each of said mandrels and said first set of condom-contacting electrode members and said second set of condom-contacting electrode members, and means to sense the status of said electrical circuit;
loading condoms onto said mandrels;
passing each of said condoms through said first set of condom-contacting electrode members and testing less than 100 percent of the circumference of each of said condoms;
sensing whether each of said condoms prevents or allows passage of electrical current through said condom;
passing each of said condoms through said second set of condom-contacting electrode members and testing less than 100 percent of the circumference of each of said condoms;
sensing whether each of said condoms prevents or allows passage of electrical current through said condom;
removing and sorting said condoms.

30. The method of claim 29, further comprising simultaneously testing a first of said condoms by said second set of condom-contacting electrode members and a second of said condoms by said first set of condom-contacting electrode members.

31. The method of claim 29, further comprising mounting said mandrels on a platform and rotating said platform to pass said condoms through said first and second sets of condom-contacting electrode members.

32. The method of claim 31, further comprising individually rotating each said mandrel about its central axis while passing said condoms through said first and second sets of condom-contacting electrode members.

33. The method of claim 29, wherein said loading step is performed manually.

34. The method of claim 29, wherein said testing step by said second set of condom-contacting electrode members comprises testing the portion of the circumference of the condoms not tested by said first set of condom-contacting electrode members.

35. The method of claim 34, wherein said testing step by said second set of condom-contacting electrode members further comprises testing at least two portions of the circumference of the condoms tested by said first set of condom-contacting electrode members.

* * * * *